United States Patent [19]
Perrin

[11] Patent Number: 5,101,837
[45] Date of Patent: Apr. 7, 1992

[54] BANDAGE ELEVATION DEVICE

[76] Inventor: Denis Perrin, 50 Alexander Street, Suite 1506, Toronto, Ont., Canada, M4Y 1B6

[21] Appl. No.: 524,878

[22] Filed: May 18, 1990

[51] Int. Cl.$^5$ .............................................. A61F 13/00
[52] U.S. Cl. .................................... 128/888; 2/16; 2/22; 602/41
[58] Field of Search ............... 128/155, 157, 165, 169, 128/171, 846, 888, 889, 892; 604/304; 2/16, 22, 454

[56] References Cited

U.S. PATENT DOCUMENTS

| 2,443,481 | 6/1948 | Sene | 128/156 |
|---|---|---|---|
| 3,141,459 | 7/1964 | Orcutt | 128/157 |
| 3,976,066 | 8/1976 | McCartney | 128/889 |
| 4,000,737 | 1/1977 | Horn | 128/888 |
| 4,159,021 | 6/1979 | Casburn | 128/889 |
| 4,905,681 | 3/1990 | Glascock | 128/157 |
| 5,003,971 | 4/1991 | Buckley | 128/156 |

FOREIGN PATENT DOCUMENTS 0000704 of 1886 United Kingdom ................ 128/888

Primary Examiner—Randall L. Green
Assistant Examiner—Paul Prebilic

[57] ABSTRACT

A bandage elevation device is provided based on two intersecting support members that are expandable in a scissors-like manner. Further articulated linkages provide a framework which, when supported by legs, will hold bandages off of wounds.

6 Claims, 2 Drawing Sheets

5,101,837

BANDAGE ELEVATION DEVICE

FIELD OF THE INVENTION

This invention relates to the protection of wounds and the promotion of healing. More particularly, this invention relates to a device for elevating a bandage over a wound.

BACKGROUND TO THE INVENTION

It has been recognized that in the case of certain types of wounds, particularly burns, it is desirable to ensure that the wound is exposed to the air to promote healing. At the same time, it is desirable to cover such wounds with bandages to prevent the wound from being dirtied and becoming infected.

Various devices for elevating bandages above a wound have been considered. U.S. Pat. No. 2,443,481 to Sene; U.S. Pat. No. 4,000,737 to Hora; and U.S. Pat. No. 4,159,021 to Casburn are exemplary. As well, Canadian patents No. 444,919 to Mathias and No. 1,050,845 to McCartney deal with this issue.

Of these references, the last to McCartney describes a lattice of criss-crossing support members, fastened by pins at their points of intersection and supported at the outer extremities along two sides on mounting pads. This grid of intersecting bars is said to be assembled in a scissors-like fashion. However, actual scissor-like movement is not possible in the configuration as depicted. At the borders of the grid McCartney shows two boundary members in the form of mounting pads into which the ends of the criss-crossing support members are shown to be attached. This attachment appears to be in the form of pins, rivets or screws, passing through circular holes.

By reason of geometric necessity, the grid of McCartney, particularly as depicted in FIG. 8, is not physically capable of being expanded and contracted. This is because attachment of the ends of the criss-crossing support members to the boundary member locks the lattice into a fixed configuration.

The present invention overcomes these deficiencies. It further enables a wound to be covered by an elevated bandage by a device which is fully adjustable in its lateral dimensions. These and further features of the invention will be apparent from the following disclosure.

SUMMARY OF THE INVENTION

In accordance with the invention, a bandage elevation device is provided which comprises an assembly of intersecting support members, terminating at free ends having separate support legs depending therefrom, and hingedly inter-connected at their points of intersection to permit the extension and contraction of the support assembly. The assembly comprises two principal support members intersecting each other about a first hinge point and four secondary support members, all of a length that is less than the length of said principal support members, wherein:

(a) the secondary support members are located in pairs on opposite sides of the intersection of the principal support members;

(b) one of the ends of each secondary member of each of said pairs is hingedly connected to an end of the other member of said pair at second hinge points; and (c) the remaining free ends of each of the secondary support members of each of said pairs being hingedly attached to one of said principal support members, to form a bridging connection between the principal support members whereby, upon rotation of the principal support members about the first hinge point, the second hinge point moves in conjunction with the ends of the principal support members to either expand or contract the width of the bandage elevation device, measured across the secondary support members, as the bridged portions of the principal support members are moved towards or away from each other or apart.

By further variation of the invention, the secondary members may be of equal length and may be attached to said principal members at points which are located distances from said intersection that are equal. Such distances may further equal the length of each of said secondary members.

These and further features of the invention will be better understood from the description of the preferred embodiment which now follows:

DESCRIPTION OF THE PREFERRED EMBODIMENTS

Figure 1:
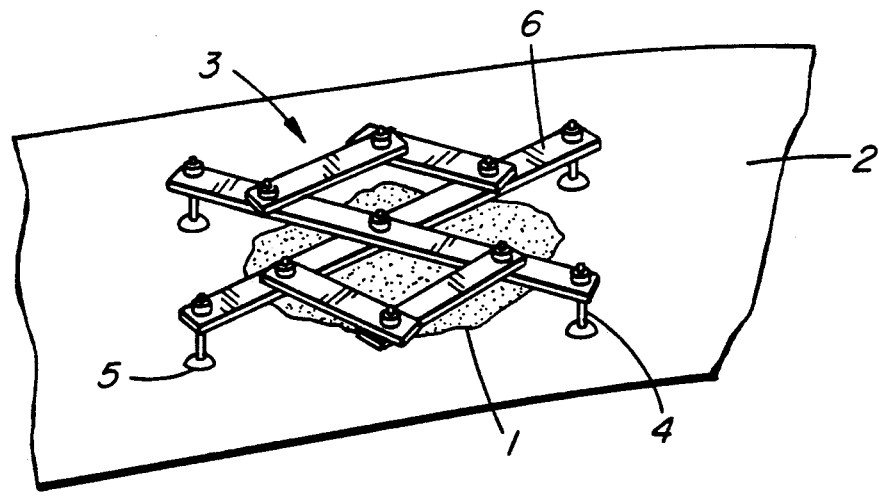
FIG. 1 is a perspective view of a bandage elevation device, according to the invention, in position over a wound.

In FIG. 1 a wound (1) is shown on an arm (2). The bandage elevation device (3) is mounted over the wound (2) supported on four legs (4).

Figure 2:
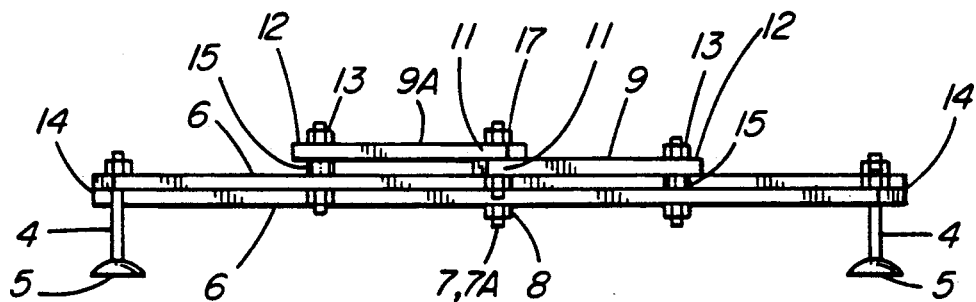
FIG. 2 is a side view of the device.

Each of the legs (4) terminates in a foot (5), best seen in FIG. 2. This foot (5) may be in the form of a soft rubber suction cup. Alternately, it may be an adhesive-carrying pad that will naturally cling to the skin.

The legs (4) are shown as short shafts descending from the principal criss-crossed support members (6). These members (6) intersect at a point of intersection (7) where a bolt or rivet (8) allows a hinging action. This provides a first hinge point; the point of intersection (7) is shown to be centrally located, but this is optional.

Figure 3:
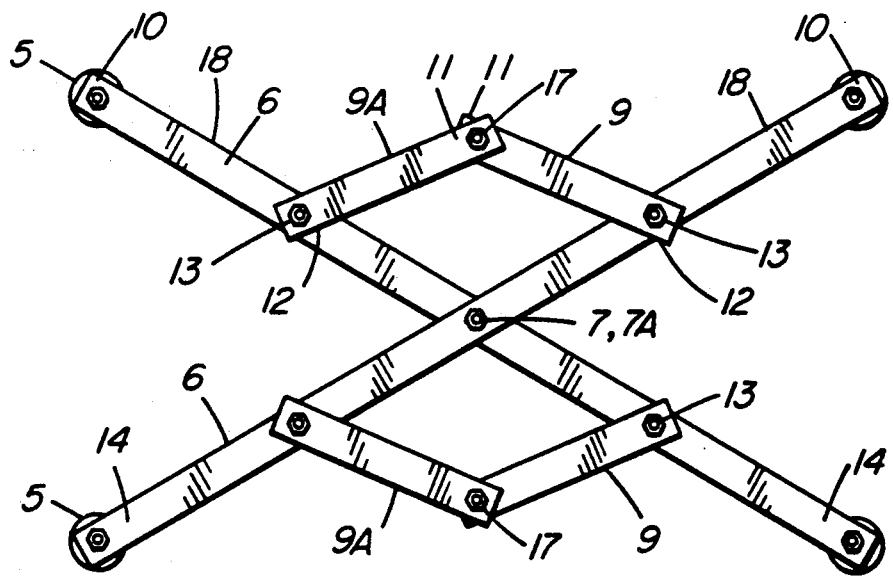
FIG. 3 is a plan view of the device.

On opposed sides of the point of intersection (7) are the secondary support members (9), best shown in FIG. 3. These secondary members (9) are of a length and are attached at points (13) to the principal members (6) so as to provide no interference to the hinging action between those members.

Each secondary member (9) is joined at one end (11) to another support member (9a). This provides a second hinge point. At the other end (12), each of the secondary support members (9) attaches to a principal member (6). The points of attachment (13) are such as to permit the hinging action and spacers (15) are employed to ensure an easy motion. Where secondary members of equal length are employed, these points of attachment (13) are all equidistant from the intersection point (7).

Figure 4:
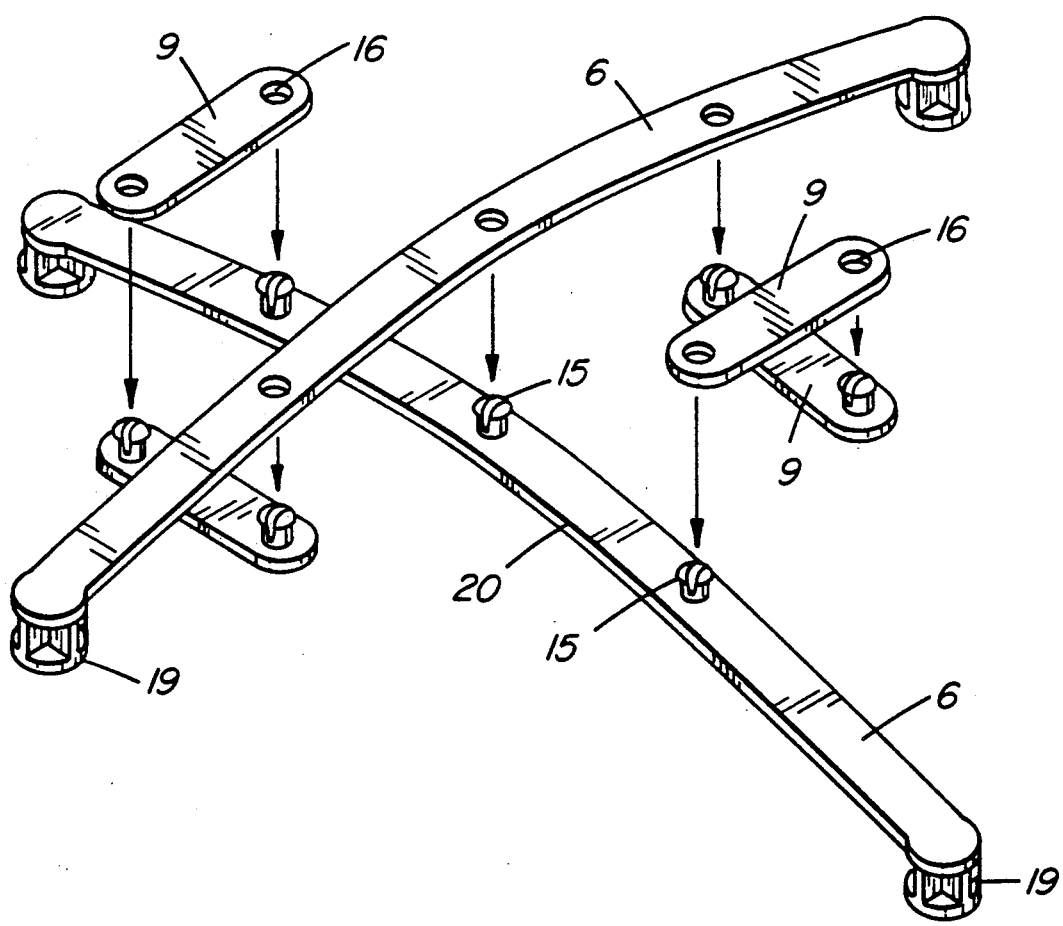
FIG. 4 is an exploded perspective view of the device showing its manner of assembly.

FIG. 4 shows an exploded assembly perspective view of the principal support members (6) and secondary support members (9).

The secondary supports (9) in FIG. 3 are shown to be one quarter of the length of the principal members (6). They are also shown to be located at attachment points

(13) which are midway between the intersection point (7) and the outer ends (14) of the principal members 6. This has been found to be of convenient proportion for cases where the bandage elevation device is expanded to an aspect ratio of 2:1 (length over width).

Set at this ratio, the common ends (11) of the secondary members (9) protrude to a point of alignment with the outer ends (14) of the principal members (6). This provides a six-point support for a bandage to be placed over a wound having an approximate aspect ratio of 2:1.

Other ratios are possible by varying the lengths of the secondary members (9) and their attachment points (13).

Alternately, perfect alignment of the ends (11) and (14) is not essential. Accordingly, a device with a designed aspect ratio of 2:1 can cover a range of adjacent ratios.

From the foregoing, it will be seen that a convenient device is provided that is light and inexpensive to produce, and will protect a wound from contact with a bandage. By means of its articulated character, a variety of shapes of wound may be covered.

The foregoing has been a description of a preferred embodiment which is intended only to be exemplary of the invention. The invention in its broadest and more specific aspects is further described and defined in the claims which now follow.

The embodiments of the invention in which an exclusive property is claimed as follows:

1. A bandage elevation device comprising:
   (a) two intersecting principal support members having non-interconnected outer ends, such principal support members being hingedly connected at their point of intersection to provide a hinge point which is the first hinge point,
   (b) separate supporting legs depending from such principal support members proximate the outer ends of the principal support members;
   (c) four secondary support members, such secondary support members having two ends each and being:
      (i) located in pairs on opposite sides of the intersection of the principal support members;
      (ii) shorter than the principal support members,
      (iii) one of the ends of each secondary support member in each pair of secondary support members being hingedly connected to an end of the other member of such pair about a second hinge point, and
      (iv) the remaining ends of each of the secondary support members in each pair being respectively hingedly attached to such principal support members to form a bridging connection between the principal support members whereby, upon rotation of the principal support members about the first hinge point, the second hinge point moves in conjunction with the ends of the principal support members to either expand or contract the width of the bandage elevation device, measured across the secondary support members, as the bridged portions of the principal support members are moved towards or away from each other or apart.

2. A device as in claim 1 wherein the second hinge point lies in substantial alignment with the ends of the principal support members.

3. A device as in claim 1 wherein the principal support members are of substantially equal length.

4. A device as in claim 3 wherein the secondary members are of substantially equal length.

5. A device as in claim 4 wherein all points of attachment between the secondary support members and the principal support members are substantially located at an equal distance from the first hinge point.

6. A device as in claim 5 wherein the second hinge point lies in substantial alignment with the ends of the principal support members.

* * * * *